United States Patent [19]

Erpenbach et al.

[11] Patent Number: 4,543,217

[45] Date of Patent: Sep. 24, 1985

[54] PROCESS FOR MAKING CARBOXYLIC ACID HALIDES

[75] Inventors: Heinz Erpenbach, Cologne; Klaus Gehrmann; Winfried Lork, both of Erftstadt; Peter Prinz, Hürth, all of Fed. Rep. of Germany

[73] Assignee: Hoechst Aktiengesellschaft, Fed. Rep. of Germany

[21] Appl. No.: 561,805

[22] Filed: Dec. 15, 1983

[30] Foreign Application Priority Data

Dec. 29, 1982 [DE] Fed. Rep. of Germany ....... 3248468

[51] Int. Cl.$^4$ ............................................. C07C 51/58
[52] U.S. Cl. ................................................ 260/544 A
[58] Field of Search ........................... 260/544 A, 549

[56] References Cited

U.S. PATENT DOCUMENTS 2,053,233  9/1936  Woodhouse .................... 260/544 A
3,632,643  1/1972  Prichard ........................ 260/544 A
4,374,070  2/1983  Larkins et al. ...................... 260/549
4,414,160  11/1983  Erpenbach et al. ............ 260/544 A Primary Examiner—Natalie Trousof
Assistant Examiner—L. Hendriksen
Attorney, Agent, or Firm—Connolly and Hutz

[57] ABSTRACT

The disclosure relates to a process for making carboxylic acid halides by reacting an alkyl halide having 1 to 6 carbon atoms or aryl halide with carbon monoxide, optionally in admixture with up to 30 volume % hydrogen, under practically anhydrous conditions at temperatures of 350 to 575 K under pressures of 1 to 300 bars in the presence of a catalyst system containing at least one noble metal belonging to group VIII of the Periodic System of the elements or its compounds, iodine and/or its compounds and optionally an inert organic solvent. To this end, the disclosure provides for use to be made of a catalyst system which additionally contains a compound of the elements belonging to groups I to III of the Periodic System, and acetic acid.

4 Claims, No Drawings

PROCESS FOR MAKING CARBOXYLIC ACID HALIDES

The present invention relates to a process for making carboxylic acid halides by reacting an alkyl halide having 1 to 6 carbon atoms or aryl halide with carbon monoxide, optionally in admixture with up to 30 volume % hydrogen, under practically anhydrous conditions at temperatures of 350° to 575° K. under pressures of 1 to 300 bars in the presence of a catalyst system containing at least one noble metal belonging to group VIII of the Periodic System of the elements or its compounds, iodine and/or its compounds, and optionally an inert organic solvent, which comprises using a catalyst system which additionally contains a compound of the elements belonging to groups I to III of the Periodic System, and acetic acid. The process should preferably be carried out in the presence of a catalyst system containing compounds of lithium and/or potassium and/or magnesium and/or calcium and/or aluminum. It has also been found advantageous to use a catalyst system which in addition to the compounds specified contains one or more compounds of the common metals Ce, Ti, Zr, Hf, Ge, Sn, Pb, V, Nb, Ta, As, Sb, Bi, Cr, Mo, W, Mn, Re, Fe, Co, Ni.

German Patent Specification De-OS 30 16 900 describes a process for making acetyl chloride by reacting methyl chloride with carbon monoxide under practically anhydrous conditions at temperatures of 350° to 575° K. under pressures of 1 to 300 bars in the presence of a catalyst system containing at least one of the noble metals rhodium, palladium, iridium or their compounds, iodine and/or its compounds, optionally trialkylphosphine oxide or triarylphosphine oxide, and an inert organic solvent which comprises using a catalyst system containing n-heptane as an inert solvent and additionally methyltrialkylphosphonium iodide and/or methyltriarylphosphonium iodide and at least one compound of chromium, molybdenum or tungsten.

German Patent Specification DE-OS 30 35 201 describes a process for making carboxylic acid halides by reacting an alkyl halide having 1 to 6 carbon atoms or aryl halide and carbon monoxide in the presence of a catalyst system containing at least one of the noble metals rhodium, palladium, iridium or their compounds, iodine and/or its compounds, methyl trialkyl- and/or methyltriarylphosphonium iodide, optionally trialkylphosphine oxide or triarylphosphine oxide and optionally in inert organic solvent, which comprises admixing the reaction mixture with 0.02 to 0.75 mol hydrogen per mol carbon monoxide. A feature of this process provides for the catalyst system to be additionally admixed with one or more compounds of the common metals Ce, Ti, Zr, Hf, Ge, Sn, Pb, V, Nb, Ta, As, Sb, Bi, Cr, Mo, W, Mn, Re, Fe, Co, Ni, as co-promoters.

By the addition of hydrogen, it is more particularly possible to ensure a constant activity for the carbonylation catalyst.

The process of this invention permits an alkyl halide or aryl halide to be subjected to carbonylation with the use of a catalyst system containing no organic phosphorus compound whatsoever which is in clear contrast with the prior art. In this invention, elements of groups I to III of the Periodic System are used as promoters which replace the organic phosphorus compound. The addition of acetic acid to the catalyst mixture however cannot be dispensed with. In this manner, a reaction system of constant activity permitting carboxylic acid halides to be obtained in good space/time-yields is obtained.

The noble metals and common metals should preferably be used in the form of their chlorides (e.g. $RhCl_3.3H_2O$, $CrCl_3.6H_2O$), acetates, carbonates, carbonyls (e.g. $[Re(CO)_5]_2$, $W(CO)_6$) or complex compounds (e.g. $[Rh(CO)_2Cl]_2$, $[Pd(CO)_2I]$.

The metal compounds belonging to groups I to III of the Periodic System of the elements should also be used in the form of their acetates, carbonates or iodides. The preferred iodine compound is methyl iodide, but ethyl iodide or hydrogen iodide can also be used.

It is also good practice to use pure acetic acid or use it in admixture with acetic anhydride.

The alkyl or aryl halides used are selected from the chlorides or bromides. As can be inferred from this, it is the corresponding carboxylic acid chlorides or bromides which are produced.

The catalyst system comprised of noble metal(-compound)/common metal(-compound)/iodine(-compound)/metal compound of groups I to III of Periodic System/acetic acid/organic solvent should preferably be used in a molar ratio of 1:(0–8):(1–100):(1–100):(50–500):(0–500).

It is also advantageous to use 0.0001–0.01 mol noble metal(-compound) and 0.05–2 mols acetic acid per mol of alkyl or aryl halide feed material.

Apart from hydrogen, it is allowable for the carbon monoxide used to contain one or more inert gases being inert under the reaction conditions, e.g. nitrogen, methane, ethane, propane. The inert solvent which is optionally used can be selected from hexane, heptane, octane, toluene, xylene or acetic anhydride.

The reaction of this invention is preferably carried out at 150° to 250° (423°–523° K.) under 20 to 180 bars, and it is possible for it to be carried out continuously or discontinuously.

EXAMPLE 1

(a) 1.38 g $RhCl_3.3H_2O$, 5.55 g $CrCl_3.6H_2O$, 6.93 g $Li(CH_3COO)$, 26.1 g methyl iodide, 102.9 g acetic acid and 105.9 g methyl chloride were introduced into an autoclave of stainless steel. First established therein was a hydrogen-partial pressure of 7.5 bars and then a CO-partial pressure of 75 bars (total pressure=82.5 bars). After a reaction period of 1 hour at 453° K., the reaction product was taken from the autoclave and analyzed. 84 g acetyl chloride (51.0% of the theoretical) was obtained; this corresponded to a space/time-yield of 338 g $CH_3COCl$ per liter reaction volume (Rv). h or catalyst efficency of 156 g $CH_3COCl$ per gram Rh . h.

(b) (Comparative experiment) 1.38 g $RhCl_3 . 3H_2O$, 5.55 g $CrCl_3 . 6H_2O$, 26.1 g methyl iodide, 102.9 g acetic acid and 105.9 g methyl chloride were introduced into an autoclave of stainless steel. First established therein was a hydrogen-partial pressure of 7.5 bars and then a CO-partial pressure of 75 bars (total pressure=82.5 bars). After a reaction period of 1 hour at 453° K., the pressure prevailing inside the autoclave was unchanged which indicated that no CO-conversion had taken place as yet. Only after temperature increase to 463° K. could a slight pressure decrease be observed in the autoclave. After a total reaction period of 4.7 hours, the reaction product was taken from the autoclave and analyzed. 23.5 g acetyl chloride (14.3% of the theoretical) was obtained; this corresponded to a space/time-yield of 21

EXAMPLE 2

1.38 g $RhCl_3 \cdot 3H_2O$, 6.93 g $Li(CH_3COO)$, 26.1 g methyl iodide, 102.9 g acetic acid and 105.9 g methyl chloride were introduced into an autoclave of stainless steel. First established therein was a hydrogen-partial pressure of 7.5 bars and then a CO-partial pressure of 75 bars (total pressure = 82.5 bars). After a reaction period of 1 hour at 453° K., the reaction product was found to contain 80.5 g acetyl chloride (48.9% of the theoretical); this corresponded to a space/time-yield of 331 g $CH_3COCl$ per liter Rv . h or catalyst efficiency of 149 g $CH_3COCl$ per g Rh . h.

EXAMPLE 3

1.38 g $RhCl_3 \cdot 3H_2O$, 10.31 g $K(CH_3COO)$, 26.1 g methyl iodide, 102.9 g acetic acid and 105.9 g methyl chloride were introduced into an autoclave of stainless steel. First established therein was a hydrogen-partial pressure of 7.5 bars and then a CO-partial pressure of 75 bars. After a reaction period of 1 hour at 453° K., the reaction product was found to contain 40 g acetyl chloride (24.3% of the theoretical); this corresponded to a space/time-yield of 162 g $CH_3COCl$ per liter Rv . h or catalyst efficiency of 74 g $CH_3COCl$ per gram Rh . h.

EXAMPLE 4

1.38 g $RhCl_3 \cdot 3H_2O$, 10.40 g $Mg(CH_3COO)_2 \cdot 4H_2O$, 26.1 g methyl iodide, 102.9 g acetic acid and 105.9 g methyl chloride were introduced into an autoclave of stainless steel. First established therein was a hydrogen partial pressure of 7.5 bars and then a CO-partial pressure of 75 bars (total pressure = 82.5 bars). After a reaction period of 1 hour at 453° K., the reaction product was found to contain 63 g acetyl chloride (38.3% of the theoretical). This corresponded to a space/time-yield of 255 g $CH_3COCl$ per liter Rv . h or catalyst efficiency of 117 g $CH_3COCl$ per gram Rh . h.

EXAMPLE 5

1.38 g $RhCl_3 \cdot 3H_2O$, 20.39 g $Ca(CH_3COO)_2 \cdot 2H_2O$, 26.1 g methyl iodide, 102.9 g acetic acid and 105.9 g methyl chloride were introduced into an autoclave of stainless steel. First established therein was a hydrogen-partial pressure of 7.5 bars and then a CO-partial pressure of 75 bars (total pressure = 82.5 bars). After a reaction period of 0.5 hour at 453° K., the reaction product was found to contain 61 g acetyl chloride (37.1% of the theoretical). This corresponded to a space/time-yield of 475 g $CH_3COCl$ per liter Rv . h or catalyst efficiency of 226 g $CH_3COCl$ per gram Rh . h.

EXAMPLE 6

1.38 g $RhCl_3 \cdot 3H_2O$, 4.69 g $ZrO(CH_3COO)_2$, 17.0 g $Al(OH)(CH_3COO)_2$, 26.1 g methyl iodide, 102.9 g acetic acid and 105.9 g methyl chloride were introduced into an autoclave of stainless steel. First established therein was a hydrogen partial pressure of 7.5 bars and then a CO-partial pressure of 75 bars (total pressure = 82.5 bars). After a reaction period of 0.5 hour at 453° K., the reaction product was analyzed and found to contain 54 g acetyl chloride (32.8% of the theoretical). This corresponded to a space/time-yield of 419 g $CH_3COCl$ per liter Rv . h or catalyst efficiency of 200 g $CH_3COCl$ per gram Rh . h.

EXAMPLE 7

1.38 g $RhCl_3 \cdot 3H_2O$, 6.24 g $[Re(CO)_5]_2$, 6.93 g $Li(CH_3COO)$, 26.1 g methyl iodide, 102.9 g acetic acid and 199.1 g methyl bromide were introduced into an autoclave of stainless steel. First established therein was a hydrogen partial pressure of 7.5 bars and then a CO-partial pressure of 75 bars (total pressure = 82.5 bars). After a reaction period of 0.75 hour at 453° K., the reaction product was found to contain 87 g acetyl bromide (33.7% of the theoretical). This corresponded to a space/time-yield of 339 g $CH_3COBr$ per liter Rv . h or catalyst efficiency of 215 g $CH_3COBr$ per gram Rh . h.

EXAMPLE 8

1.38 g $RhCl_3 \cdot 3H_2O$, 5.56 g vanadylacetyl acetonate $[VO(C_5H_7O_2)_2]$, 17.0 g $Al(OH)(CH_3COO)_2$, 26.1 g methyl iodide, 102.9 g acetic acid and 129 g ethyl chloride were introduced into an autoclave of stainless steel. First established therein was a hydrogen partial pressure of 7.5 bars and then a CO-partial pressure of 75 bars (total pressure = 82.5 bars). After a reaction period of 3 hours at 458° K., the reaction product was found to contain 15 g propionyl chloride (8.1% of the theoretical). This corresponded to a space/time-yield of 18 g $CH_3CH_2COCl$ per liter Rv . h or catalyst efficiency of 9.3 g $CH_3CH_2COCl$ per gram Rh . h.

EXAMPLE 9

1.38 g $RhCl_3 \cdot 3H_2O$, 3.55 g $Ni(CO)_4$, 10.20 g $Ca(CH_3COO)_2 \cdot 2H_2O$, 26.1 g methyl iodide, 102.9 g acetic acid and 113.9 g benzyl chloride were introduced into an autoclave of stainless steel. First established therein was a hydrogen-partial pressure of 7.5 bars and then a CO-partial pressure of 75 bars (total pressure = 82.5 bars). After a reaction period of 1 hour at 453° K., the reaction product was analyzed and found to contain 44.5 g phenylacetic acid chloride (32.0% of the theoretical). This corresponded to a space/time-yield of 172 g $C_6H_5CH_2COCl$ per liter Rv . h or catalyst efficiency of 83 g $C_6H_5CH_2COCl$ per gram Rh . h.

EXAMPLE 10

1.11 g $PdCl_2 \cdot 2H_2O$, 4.69 g $ZrO(CH_3COO)_2$, 20.39 g $Ca(CH_3COO)_2 \cdot 2H_2O$, 26.1 g methyl iodide, 102.9 g acetic acid and 105.9 g methyl chloride were introduced into an autoclave of stainless steel. First established therein was a hydrogen-partial pressure of 7.5 bars and then a CO-partial pressure of 75 bars (total pressure = 82.5 bars). After a reaction period of 1 hour at 453° K., the reaction product was found to contain 47 g acetyl chloride (28.6% of the theoretical). This corresponded to a space/time-yield of 180 g $CH_3COCl$ per liter Rv . h or catalyst efficiency of 85 g $CH_3COCl$ per gram Pd . h.

EXAMPLE 11

1.56 g $IrCl_3$, 6.93 g $Li(CH_3COO)$, 26.1 g methyl iodide, 102.9 g acetic acid and 105.9 g methyl chloride were introduced into an autoclave of stainless steel. First established therein was a hydrogen-partial pressure of 7.5 bars and then a CO-partial pressure of 75 bars (total pressure = 82.5 bars). After a reaction period of 3 hours at 463° K., the reaction product was found to contain 31 g acetyl chloride (18.8% of the theoretical). This corresponded to a space/time-yield of 42.5 g $CH_3COCl$ per liter Rv . h or catalyst efficiency of 10.3 g $CH_3COCl$ per gram Ir . h.

EXAMPLE 12

1.38 g RhCl$_3$ . 3H$_2$O, 6.93 g Li(CH$_3$COO), 26.1 g methyl iodide, 52 g acetic acid, 52 g acetic anhydride and 105.9 g methyl chloride were introduced into an autoclave of stainless steel. First established threin was a hydrogen-partial pressure of 7.5 bars and then a CO-partial pressure of 75 bars (total pressure=82.5 bars). After a reaction period of 1 hour at 453° K., the reaction product was analyzed and found to contain 85 g acetyl chloride (51.6% of the theoretical). This corresponded to a space/time-yield of 348 g CH$_3$COCl per liter Rv . h or catalyst efficiency of 158 g CH$_3$COCl per gram Rh . h.

We claim:

1. A process for making carboxylic acid halides by reacting an alkyl halide having 1 to 6 carbon atoms or aryl halide or benzyl chloride with carbon monoxide optionally containing up to 30 volume % hydrogen under practically anhydrous conditions at temperatures of 350° to 575° K. under pressures of 1 to 300 bars in the presence of a catalyst system containing at least one noble metal belonging to Group VIII of the Periodic System of the elements or its compounds, iodine and/or its compounds, optionally at least one compound selected from the non-noble metals Ce, Ti, Zr, Hf, Ge, Sn, Pb, V, Nb, Ta, As, Sb, Bi, Cr, Mo, W, Mn, Re, Fe, Co or Ni and optionally an inert organic solvent which comprises using a catalyst system essentially free of organic phosphorus compounds which additionally contains a compound of the elements belonging to groups I to III of the Periodic System and acetic acid, the amount of acetic acid included in the catalyst system being about 50-500 moles per mole of said noble metal or its compounds.

2. A process as claimed in claim 1, wherein the catalyst system contains at least one compound selected from the metals lithium, potassium, magnesium, calcium or aluminum.

3. A method as claimed in claim 1 wherein a C$_1$-C$_6$ alkyl or aryl-substituted C$_1$-C$_6$ alkyl chloride or bromide is reacted with a coreactant consisting essentially of carbon monoxide in the presence of said catalyst system to obtain the corresponding carboxylic acid chloride or bromide.

4. A process as claimed in claim 1, wherein said catalyst system contains the noble metal compound/non-noble metal compound/iodine or iodine compound/metal compound of groups I to III/acetic acid/organic solvent in the molar ratio of 1:(0-8):(1-100):(1-100):(50-500):(0-500), the amount of acetic acid, determined with respect to the alkyl or aryl halide or benzyl chloride feed material, being 0.05-2 moles per mole of said feed material.

* * * * *